United States Patent
Taylor et al.

(10) Patent No.: US 9,173,944 B2
(45) Date of Patent: *Nov. 3, 2015

(54) FORMULATION SUITABLE FOR STABILIZING PROTEINS, WHICH IS FREE OF MAMMALIAN EXCIPIENTS

(75) Inventors: Harold Victor Taylor, Frankfurt am Main (DE); Gerd J. Mander, Frankfurt am Main (DE); Markus Burger, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 1 day.

This patent is subject to a terminal disclaimer.

(21) Appl. No.: 13/878,629

(22) PCT Filed: Oct. 11, 2011

(86) PCT No.: PCT/EP2011/005088
§ 371 (c)(1),
(2), (4) Date: Apr. 10, 2013

(87) PCT Pub. No.: WO2012/048854
PCT Pub. Date: Apr. 19, 2012

(65) Prior Publication Data
US 2013/0224248 A1    Aug. 29, 2013

Related U.S. Application Data

(60) Provisional application No. 61/404,915, filed on Oct. 12, 2010.

(30) Foreign Application Priority Data

Oct. 12, 2010    (EP) ..................... 10013567

(51) Int. Cl.

| | |
|---|---|
| *A61K 9/00* | (2006.01) |
| *A61K 39/00* | (2006.01) |
| *A61K 39/08* | (2006.01) |
| *A61K 47/36* | (2006.01) |
| *A61K 9/19* | (2006.01) |
| *A61K 47/14* | (2006.01) |
| *A61K 47/26* | (2006.01) |
| *A61K 47/32* | (2006.01) |

(52) U.S. Cl.
CPC .............. *A61K 47/36* (2013.01); *A61K 9/0019* (2013.01); *A61K 9/19* (2013.01); *A61K 39/08* (2013.01); *A61K 47/14* (2013.01); *A61K 47/26* (2013.01); *A61K 47/32* (2013.01); *A61K 39/00* (2013.01)

(58) Field of Classification Search
CPC ......... A61K 9/00; A61K 31/00; A61K 47/00; A61K 47/10; A61K 47/26
USPC ........................................................ 424/400
See application file for complete search history.

(56) References Cited

U.S. PATENT DOCUMENTS

| | | |
|---|---|---|
| 5,955,105 A | 9/1999 | Mitra et al. |
| 6,447,806 B1 | 9/2002 | Gassman et al. |
| 2006/0018931 A1 | 1/2006 | Taylor |
| 2006/0205661 A1 | 9/2006 | Besman et al. |
| 2007/0122476 A1 | 5/2007 | Hanshew et al. |
| 2007/0134199 A1 | 6/2007 | Frevert |
| 2008/0145430 A1 | 6/2008 | Panmai |
| 2008/0286280 A1 | 11/2008 | Kallmeyer |
| 2009/0155314 A1 | 6/2009 | Tezel et al. |

FOREIGN PATENT DOCUMENTS

| | | |
|---|---|---|
| FR | 2881139 | 7/2006 |
| JP | 2001-503781 | 3/2001 |
| JP | 2004043475 | 2/2004 |
| JP | 2007-537274 | 12/2007 |
| JP | 2008-507581 | 3/2008 |
| WO | WO0074703 | 12/2000 |
| WO | WO0158472 | 8/2001 |
| WO | WO2004006954 | 1/2004 |
| WO | WO2006005910 | 1/2006 |
| WO | WO2006027207 | 3/2006 |
| WO | WO 2006 062875 | 6/2006 |
| WO | WO 2006/079722 | 9/2006 |
| WO | WO2006114308 | 11/2006 |
| WO | WO 2007/041664 | 4/2007 |
| WO | WO2008029908 | 3/2008 |
| WO | WO2009008595 | 1/2009 |
| WO | WO2009015840 | 2/2009 |
| WO | WO2010048275 | 4/2010 |

OTHER PUBLICATIONS

International Search Report and Written Opinion for PCT/EP2011/005088 of Apr. 5, 2012.
Carpenter, et al., Pharmaceutical Biotechnology, vol. 13, p. 109, 133, Jan. 2002.
European search report with written opinion for EP09005470 of Oct. 12, 2009.
Goschel, et al., Experimental Neurology, vol. 147, p. 96-102, 1997.
International search report with written opinion for PCT/EP2010/002360 of May 19, 2010.
Montecucco, C., et al., Arch Toxicol. vol. 18 (suppl.), p. 342-354, 1996.
Office Action dated Jan. 7, 2014 from Japanese application 2012-505092 with translation.
Office Action dated Jan. 23, 2014 from Chinese appiication 201080016527.6 with English translation.
Office Action, dated Oct. 23, 2012 from Chinese Application No. 201080016257.6 with translation.
Office Action dated Feb. 14, 2014 from Russian application No. 2011146541/15(069722) translation.
ROMPP Chemie Lexikon, 9. Auflage (1995), Thieme Verlag, p. 5165, Right column.
Simpson, L.L., Annu. Rev. Pharmaxological Toxicology, vol. 44, p. 167-193, 2004.
Japanese Office Action for JP2013-533125 dated May 1, 2015.
Translation of Japanese Office Action for JP2013-533125 dated May 1, 2015.

*Primary Examiner* — Rodney P Swartz
(74) *Attorney, Agent, or Firm* — Hueschen and Sage

(57) ABSTRACT

A formulation free of protein which stabilizes pharmaceutical active proteins, peptides, or mixtures thereof in large scale production processes comprising a mixture of a hydrophilic polymer and a non-ionic detergent, and a mixture of a polyalcohol and a sugar. In some embodiments the polyalcohol is absent.

15 Claims, 2 Drawing Sheets

Figure 2:
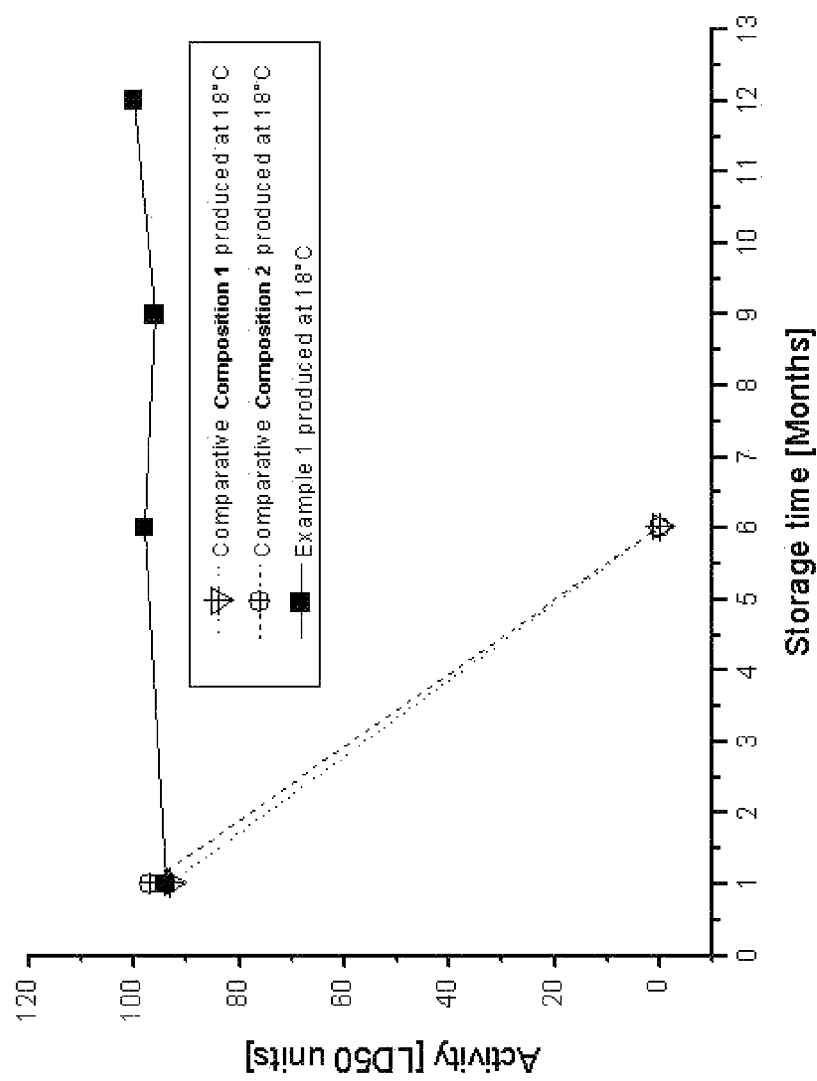

Figure 1

FORMULATION SUITABLE FOR STABILIZING PROTEINS, WHICH IS FREE OF MAMMALIAN EXCIPIENTS

FIELD OF THE INVENTION

The present invention pertains to a formulation for stabilizing proteins, peptides or mixtures thereof when produced under large scale industrial production processes, wherein said formulation is free of stabilizing proteins. In particular, it pertains to a formulation comprising a hydrophilic polymer, a sugar, and a detergent which is present in an amount between 0.2 and 0.01 mg/g, and wherein the formulation is free of stabilising proteins. In one embodiment, the present invention relates to a kit, wherein said kit comprises one or more containers comprising the said formulation/composition, instructions for use and, optionally, a pharmaceutically acceptable sterile solvent.

BACKGROUND OF THE INVENTION

Protein formulations, which are free of stabilizing proteins are known in the art. WO 2006/020208 relates to pharmaceutical compositions comprising Botulinum toxin and a non-proteinaceous stabilizing agent, which retains the activity of the Botulinum toxin in an aqueous solution.

WO 2006/005910 relates to solid or liquid pharmaceutical compositions comprising Botulinum toxin complex or high purity Botulinum toxin and a surfactant. A maximum of six months stability at 23° C. to 27° C. is reported therein.

WO 2007/041664 relates to a pharmaceutical composition comprising a Botulinum toxin and a polyvinylpyrollidone (PVP) and optionally a disaccharide.

WO 2004/006954 relates to a pharmaceutical composition comprising a stabilized Botulinum toxin and at least one enhancing agent for facilitating transdermal delivery of the Botulinum toxin into a human patient by enhancing the permeability of the patient's skin.

WO 01/58472 discloses a pharmaceutical composition suitable for injection into a human patient, comprising a Botulinum toxin and a polysaccharide. It also discloses a pharmaceutical composition comprising a neurotoxin and hydroxyethyl starch.

WO 2006/079722 relates to the use of liquid compositions for implementing the method of freeze-drying proteins, to stabilize said proteins, said compositions comprising; a filler agent having a collapse temperature between $-18°$ C. and $0°$ C., a stabilizer, a buffer solution, and, as the case may be, a nonionic surfactant.

European application 09005470.1-1219 also relates to stable compositions free of HSA.

US 2007/122476 A1 (Hanshew Dwight D. JR. et al.), 31. May 2007, (2007 May 31) refers to a thyroid hormone (thyroxine) stabilized by a formulation comprising microcrystalline cellulose, mannitol, sucrose and lauryl sulfate as a detergent.

WO 2007/041664 (Allergan, Inc.), 12 Apr. 2007 (2007 Apr. 12), refers to a lyophilized formulation comprising Botulinum toxin, PVP, sucrose or mannitol and Poloxamer 188.

FR 2 881 139 (Agronomique Inst. Nat. Rech.), 28 Jul. 2006 (2006-07-28), refers to formulations comprising in one case protein, mannitol, PVP and TRIS HCI; in another case protein, glycine, PVP and TRIS HCI; and in a third case protein, maltodextrine, saccharose, Polysorbate 80 and TRIS HCI The present invention, however, refers to certain formulations which result in even more stable formulations rendering them especially suitable when produced under large scale industrial production processes.

OBJECTS OF THE INVENTION

An object of the present invention was to provide novel formulations for stabilizing proteins, which are free of stabilizing proteins. Such formulations may be formulated such that they provide superior stability to proteins, compared to formulations of the prior art.

Furthermore, the novel formulations of the present invention result in stable formulations when produced under large scale industrial production processes.

This and other objects were achieved by the formulation being the subject of this application.

SUMMARY OF THE INVENTION

In one embodiment the present invention encompasses a formulation free of proteins in particular free of stabilizing proteins such as animal or human serum albumin (HSA), gelatine, amino acids such as histidine, lysine, methionine or immunoglobulins; which stabilizes pharmaceutical active proteins, peptides, or mixtures thereof in large scale production processes comprising a mixture of a hydrophilic polymer and a non-ionic detergent, wherein the weight ratio between the hydrophilic polymer and the detergent is from 18:1 to 22:1 (wt-%), a mixture of a polyalcohol and a sugar, wherein the weight ratio of polyalcohol to sugar is from 2:1 to 5:1 (wt-%), and wherein the non-ionic detergent is present in said formulation in an amount between 0.2 and 0.01 mg/g.

The term "free of proteins" hereinunder refers to a formulation which is free of any protein and/or peptide which is not the pharmaceutical active protein, peptide or mixture of thereof. In particular it is meant that the formulation is free of stabilizing proteins such as animal or human serum albumin (HSA), gelatine, amino acids such as histidine, lysine, methionine and/or immunoglobulins.

The term "a formulation which stabilizes pharmaceutical active proteins, peptides, or mixtures thereof" hereinunder refers to a formulation which is capable of stabilizing a pharmaceutical active protein, peptide or mixture thereof. Therein the term "stabilizing" refers to an elongation of the pharmaceutical activity of the pharmaceutical active protein, peptide or mixture thereof, for example the $LD_{50}$-activity of the neurotoxic component of a Botulinum toxin, when compared to said pharmaceutical active protein, peptide or mixture thereof without any stabilizing means, such as HSA.

The term "pharmaceutical composition" as used within the subject application refers to the combination of the formulations free of proteins and a pharmaceutically active protein, peptide or mixture thereof.

In another embodiment the present invention encompasses a formulation free of proteins in particular free of stabilizing proteins such as animal or human serum albumin (HSA), gelatine, amino acids such as histidine, lysine, methionine or immunoglobulins; which stabilizes pharmaceutical active proteins, peptides, or mixtures thereof in large scale production processes comprising a mixture of a hydrophilic polymer and a non-ionic detergent, wherein the weight ratio between the hydrophilic polymer and the detergent is from 2:1 to 10:1 (wt-%), and wherein the non-ionic detergent is present in said formulation in an amount between 0.2 and 0.01 mg/g; a sugar; and wherein no polyalcohol is present.

In yet further embodiments the above mentioned hydrophilic polymer is selected from the group consisting of hyaluronic acid, polyvinylpyrollidone (PVP), copolymers of N-vinylpyrollidone, a cellulose derivative, wherein said cellulose derivative is selected from the group consisting of hydroxypropyl methyl cellulose, hydroxypropyl cellulose, hydroxyethyl cellulose, methyl cellulose, carboxymethyl cellulose, dextran, Polyethyleneglycol (PEG), PEG/PPG block copolymers, homo- and copolymers of acrylic and methacrylic acid, polyurethanes, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, and mixtures thereof.

In further embodiments the above mentioned polyalcohol is selected from the group consisting of mannitol, inositol, lactilol, isomalt, xylitol, erythritol, sorbitol, and mixtures thereof.

In again further embodiments the above mentioned sugar is selected from the group consisting of monosaccharides, disaccharides, polysaccharides, and mixtures thereof.

The present invention also encompasses a use of any of the above mentioned formulations for stabilising pharmaceutically active proteins, peptides, or mixtures thereof.

In one further embodiment, the present invention pertains to a composition comprising any of the above mentioned formulations which further comprises a pharmaceutically active peptide, a protein—naturally occurring or modified/artificial—or a mixture thereof.

In one further embodiment the composition of the invention is lyophilised.

In even a further embodiment above mentioned composition according comprises a pharmaceutically active protein which is selected from the group consisting of toxins, chondroitin, elastin, actin, myosin, aprotinin, growth hormone, growth hormone releasing factor, parathyroid hormone, thyroid stimulating hormone, lipoproteins (LDL, IDL, VLDL, VHDL, HDL), apolipoproteins (ApoA-1, ApoA-II, ApoA-IV, ApoC-I, ApoC-II, ApoC-Ill, ApoD, ApoE), α-1 Antitrypsin, insulin, proinsullin, follicle stimulating hormone, calcitonin, oxytocin, vasopressin, leuprolide acetate, somatostatin, luteinizing hormone, glucagons, clotting factors, anti-clotting factors, plasminogen activator, human macrophage inflammatory protein, vascular endothelin growth factor (VEGF), rheumatoid factors, bone derived neurotrophic factor (BDNF), nerve growth factor-β (NGF-β), platelet-derived growth factor (PDGF), fibroblast growth factor (FGF), epidermal growth factor (EGF), transforming growth factor (TGF-β1, TGF-β2, TGF-β3, TGF-β4, TGF-β5), erythropoietin, interleukins (IL-1 to IL-10), bone morphogenic protein (BMP) parathyroid hormone, DNAse, cationic ferritin, interferon (α, β, γ) and mixtures thereof. In yet a further embodiment above mentioned composition comprises a pharmaceutically active protein which is selected from the group consisting of Botulinum toxin, diphtheria toxin, tetanus toxin and mixtures thereof. In further embodiments the above mentioned composition comprises Botulinum toxin, hyaluronic acid, mannitol, sucrose, polysorbate 80 and optionally water for injection. In another embodiment, said composition is an injectable solution.

A further aspect of the present invention relates to a composition comprising a peptide or a protein, or a mixture thereof, as defined herein, for use as a medicament, a cosmetic product, a cosmeceutical product or a diagnostic product. In a further embodiment said composition is suitable for the treatment of a disease or condition caused by or associated with hyperactive cholinergic innervation of muscles or exocrine glands in a patient.

A further aspect of the present invention relates to a kit comprising one or more containers comprising the above mentioned formulations and/or compositions and instructions for use of said formulation, and optionally a pharmaceutically acceptable sterile solvent.

The objects of the invention were achieved by the formulation being subject of this application. The present invention pertains to a formulation comprising a mixture of a hydrophilic polymer and a detergent, wherein the weight ratio between the hydrophilic polymer and the detergent is from [18:1] to [22:1] (wt-%), e.g. [18:1], [19:1], [20:1], [21:1] or [22:1]; a mixture of a polyalcohol and a sugar, wherein the weight ratio of polyalcohol to sugar is from [2:1] to [5:1] (wt-%), e.g. [2:1], [2.5:1], [3:1], [3.5:1], [4:1], [4.5:1] or [5:1] and wherein the formulation is free of stabilising proteins.

In another embodiment the formulation comprises a mixture between a hydrophilic polymer and a detergent, wherein the weight ratio between the hydrophilic polymer and the detergent is from [2:1] to [30:1] (wt-%), e.g. [2:1], [3:1], [4:1], [6:1], [7:1]; [8:1], [9:1], [10:1], [15:1], [20:1], [25:1] and [30:1]; and a sugar, and wherein the formulation is free of stabilising proteins and polyalcohols, such as mannitol, inositol, lactilol, isomalt, xylitol, erythritol and sorbitol. In one embodiment the composition comprising ≤1.6 ng neurotoxic component of Botulinum toxin, 1.0 mg of hyaluronic acid, 10.0 mg of sucrose and 0.2 mg of Polysorbate 80 is excluded.

DETAILED DESCRIPTION OF THE INVENTION

The present invention pertains to a formulation comprising a mixture of a hydrophilic polymer and a detergent, wherein the weight ratio between the hydrophilic polymer and the detergent is from [18:1] to [22:1] (wt-%), e.g. [18:1], [19:1], [20:1], [21:1] or [22:1]; a mixture of a polyalcohol and a sugar, wherein the weight ratio of polyalcohol to sugar is from [2:1] to [5:1] (wt-%), e.g. [2:1], [2.5:1], [3:1], [3.5:1], [4:1], [4.5:1], [5:1] and wherein the formulation is free of stabilising proteins.

In one embodiment the present invention pertains to a formulation comprising a formulation free of proteins, in particular stabilising proteins which is stable in large scale production processes comprising a mixture of a hydrophilic polymer and a non-ionic detergent, wherein the weight ratio between the hydrophilic polymer and the detergent is 20:1 (wt-%), a mixture of a polyalcohol and a sugar, wherein the weight ratio of polyalcohol to sugar is 3:1 (wt-%), and wherein the non-ionic detergent is present in said formulation in an amount of either 0.2 or 0.1 mg/g.

In another embodiment the formulation comprises a mixture between hydrophilic polymer and a detergent, wherein the weight ratio between the hydrophilic polymer and the detergent is from [2:1] to [30:1] (wt-%), e.g. [2:1], [3:1], [4:1], [5:1] [6:1], [7:1]; [8:1], [9:1], [10:1], [15:1], [20:1], [25:1] and [30:1]; and a sugar, and wherein the formulation is free of stabilising proteins and polyalcohols, such as mannitol, inositol, lactilol, isomalt, xylitol, erythritol and sorbitol. In one embodiment the composition comprising ≤1.6 ng neurotoxic component of Botulinum toxin, 1.0 mg of hyaluronic acid, 10.0 mg of sucrose and 0.2 mg of Polysorbate 80 is excluded.

In one further embodiment, the present invention pertains to a composition that comprises one of said formulations and a peptide, a protein or a mixture thereof, naturally occurring or modified/artificial.

The term "formulation" as used herein relates to a mixture comprising pharmaceutically acceptable excipients and encompasses liquid, solid, semisolid, colloidal and all other forms known to the person skilled in the art. The said formulation herein is free of stabilizing proteins.

The term "large scale industrial production processes" refers to production processes of large amounts of standardized products, including and especially on assembly lines. A clear boundary between laboratory-size and large scale production processes is not always easy to draw. Therefore, within this invention, a production process is considered "large scale" if at least one of the following features apply:

A production process which is not anymore accomplishable by one single skilled person, but need at least two or more skilled persons taking care of different specialized parts of the full production process;

A significant increase of the production volumes or weights as compared to the mere "proof-of-principle" experiments i.e. volumes or weights are increased by at least one order of magnitude in comparison to laboratory-size "proof-of-principle" experiments;

A production process which leads directly to the production of the subject-matter to be sold, e.g. the final formulation to be marketed, sold and applied by the physician;

A production process which can be carried out by averagely trained workers of the field instead of skilled experts;

A production process which needs considerable more time as compared to the mere "proof-of-principle" experiments i.e. especially the storage times before, during and/or after the production process are increased by at least a factor of two in comparison to laboratory-size "proof-of-principle" experiments.

The term "composition" or "pharmaceutical composition" as used in the instant invention relates to a formulation as claimed herein which further comprises a peptide, a protein or a mixture thereof.

The formulation of the invention comprises a mixture of a hydrophilic polymer and a detergent, wherein the weight ratio between the hydrophilic polymer and the detergent is from [18:1] to [22:1] (wt-%), e.g. [18:1], [19:1], [20:1], [21:1] or [22:1].

The term "polymer" as used herein relates to structures composed of repeating units. The term "polymer" within the scope of the instant invention is employed both for homopolymers and copolymers.

The term "hydrophilic" as used herein relates to substances, materials, excipients or pharmaceutically active ingredients which are wettable by water.

In one embodiment of the present invention, the hydrophilic polymer is selected from the group consisting of hyaluronic acid, polyvinylpyrollidone (PVP), copolymers of N-vinylpyrollidone, cellulose derivatives, Polyethyleneglycol (PEG), PEG/PPG block copolymers, homo- and copolymers of acrylic and methacrylic acid, polyurethanes, polyvinyl alcohol (PVA), polyvinylethers, maleic anhydride based copolymers, polyesters, vinylamines, polyethyleneimines, polyethyleneoxides, poly(carboxylic acids), polyamides, polyanhydrides, polyphosphazenes and mixtures thereof.

The said cellulose derivative may be selected from the group consisting of hydroxypropyl methyl cellulose, hydroxypropyl cellulose, hydroxyethyl cellulose, methyl cellulose, carboxymethyl cellulose, dextran, and mixtures thereof.

The term "polyvinylpyrrolidone" as used herein refers to a water-soluble polymer made from the monomer N-vinylpyrrolidone. The terms and abbreviations "PVP, povidone, polyvidone, crospovidone, Kollidone" are used synonymously.

The said polyvinylpyrrolidone (PVP) may be Kollidon 12 PF, Kollidon 17 PF, Kollidon 25, Kollidon 30, Kollidon 90 F, povidone, crospovidone, Kollidon VA 64 and copovidone or a mixture thereof.

The term "hyaluronic acid" within the meaning of the instant invention refers to a non-sulfated glycosaminoglycan.

In one embodiment the hyaluronic acid has a molecular weight of 0.8 to $1.2 \times 10^6$ Da. Furthermore, within the present invention also crosslinked hyaluronic acid may be used. The term "hyaluronic acid" is used synonymously with the term "hyaluronan". Within the present invention the term "hyaluronic acid" also encompasses derivatives of hyaluronic acid, such as salts thereof, e.g. sodium, potassium, magnesium and calcium salts. Further the term "hyaluronic acid" encompasses all natural and synthetic derivates thereof. It is a molecule having typically a molecular weight of 10 kDa and $4.5 \times 10^6$ Da.

The formulation of the invention comprises in one embodiment a mixture of polyalcohol and sugar in a weight ratio of from [2:1] to [5:1] (wt. %).

With the term "polyalcohol" as used herein a group of carbohydrate-based ingredients is meant, which are employed to protect the protein against instability. The term "polyol" and "sugar alcohols" are used synonymously. Examples for polyalcohols as envisaged in the compositions of the invention are mannitol, inositol, lactitol, isomalt, xylitol, erythritol and sorbitol.

The term "sugar" as used herein relates to any monosaccharide, disaccharide and polysaccharide. The term "monosaccharide" as used herein relates to the basic units of carbohydrates. All "monosaccharides" envisaged by the present invention have the formula $C_nH_{2n}O_n$ (n is between 3 and 7). The term "disaccharide" within the scope of the present invention relates to carbohydrates composed of two monosaccharides. The term "polysaccharides" as used herein relates to repeating units of monosaccharides, wherein the monosaccharides are bound with glycosidic bonds. Examples for sugars as envisaged in the compositions of the invention are glucose, sucrose, lactose, dextrose, maltose and fructose. The acyclic mono- and disaccharides contain either aldehyde groups or ketone groups.

In one further embodiment of the present invention the sugar is selected from the group consisting of monosaccharides, wherein said monosaccharides may be glucose, thioglucose, thiomannose, thiofructose, fructose and galactose. In another embodiment the sugar is a disaccharide, wherein said disaccharide may be trehalose, sucrose, octa-O-acetyl-thiotrehalose, thiosucrose, thiomaltose, maltose, and maltitol. In one further embodiment the sugar is a polysaccharide, wherein said polysaccharide may be an alginate, hydroxyethyl starch and hydroxypropyl starch.

The term "mixture" as used herein relates to compositions of homogeneous or heterogeneous nature, wherein at least two substances of the same or different composite or structure are mixed by employing the methods and devices known to the person skilled in the art. The term "mixture" within the scope of the instant invention encompasses mixtures in solid, liquid and semisolid form.

The term "mixing" as used herein relates to combining at least two active or inactive ingredients at various proportions. Mixing relates to any process or action which combines also at least two different active or inactive substances from the same group or from different groups, in any sequential order. The term "mixing" also discloses any process or action which combines any active ingredient with any excipient.

The present invention claims in one embodiment a formulation, wherein a polyalcohol and a sugar are mixed to obtain a mixture of polyalcohol and sugar at a weight ratio of [2:1] to [5:1]. In one further embodiment said mixture of polyalcohol and sugar is at a weight ratio of [2:1] to [3:1], e.g. [2:1], [2.5:1], [3:1]. In another embodiment said mixture of polyalcohol and sugar is at a weight ratio of [3:1].

According to one embodiment of the instant invention the mixture of polyalcohol and sugar comprises mannitol and sucrose at a weight ration of [2:1] to [5:1], e.g. [2:1], [2.5:1], [3:1], [3.5:1], [4:1], [4.5:1], [5:1]. In one further embodiment of the instant invention the mixture of polyalcohol and sugar comprises mannitol and sucrose at a weight ration of [3:1].

Said polyalcohol and said sugar may be mixed by using V-blenders (twin shell blenders), rotary drum mixers, double ribbon blenders, plow mixers, paddle mixers, double cone blenders. The skilled person will be able to select the correct mixer depending on bench-top scale or high scale. The mixing time will depend on the batch size, quality of excipients, e.g. particle size of the powder and the mixer type.

The formulation of the invention also comprises a detergent.

The term "detergent" as used herein relates to any substance employed to solubilize or stabilize another substance, which may be either a pharmaceutical active ingredient or another excipient in a formulation. Said detergent may stabilize said protein or peptide either sterically or electrostatically. The term "detergent" is used synonymously with the terms "surfactants" or "surface active agents".

In one embodiment of the present invention the detergent is selected from the group consisting of non-ionic surfactants.

The term "non-ionic surfactants" within the meaning of the instant invention refers to surfactants having no positive or negative charge.

According to one aspect said non-ionic surfactants may be sorbitan esters (sorbitan monolaurate, sorbitan monopalmitate, sorbitan monostearate, sorbitan tristearate, sorbitan monooleate, Sorbitan trioleate), polysorbates (polyoxyethylene (20) sorbitan monolaurate (Polysorbate 20), polyoxyethylene (20) sorbitan monopalmitate, polyoxyethylene (20) Sorbitan monostearate, polyoxyethylene (20) sorbitan tristearate, polyoxyethylene (20) Sorbitan trioleate, Polyoxyethylen(20)-sorbitan-monooleate (Tween 80/Polysorbate 80)), poloxamers (poloxamer 407, poloxamer 188), cremophor, and mixture thereof.

In another embodiment said detergent is anionic surfactant.

The term "anionic surfactant" within the meaning of the present invention refers to surfactants comprising an anionic hydrophilic group.

According to one aspect said anionic surfactant may be tetradecyltrimethylammonium bromide, dodecyltrimethylammonium bromide, sodium laureth sulphate, sodium dodecyl sulphate (SDS), cetrimide, hexadecyltrimethylammonium bromide, and a mixture thereof.

In one further embodiment said detergent is a cationic surfactant.

The term "cationic surfactant" within the meaning of the instant invention encompasses surfactants comprising an cationic hydrophilic group.

According to one aspect said cationic surfactant may be benzalkonium chloride, cetyl trimethylammonium bromide (CTAB), cetylpyridinium chloride (CPC), benzethonium chloride (BZT), and mixtures thereof.

In one embodiment of the present invention the concentration of the detergent is not more than 0.2 mg/g based on the total weight of the production bulk composition, i.e. the total amount of the formulation of the invention, the peptide or protein to be stabilized and the sterile solvent added for injection, typically water or an isotonic saline solution. In one further embodiment of the instant invention, the concentration of the detergent is between 0.1 mg/g and 0.2 mg/g based on the total weight of the production bulk composition. In another embodiment of the instant invention the detergent employed is Polysorbate 80 and the concentration thereof is in one embodiment 0.2 mg/g and in another embodiment 0.1 mg/g based on the total weight of the production bulk composition. In none of the embodiments the concentration of the detergent is below 0.01 mg/g.

It has been found that a reduction in the concentration of the detergent below 0.2 mg/g results in the surprising finding of an increased stability of the neurotoxin, whereas the complete absence of detergent renders the formulation again less stable. The most stable formulation therefore can be found between 0.01 mg/g and 0.2 mg/g, in some embodiments at 0.1 mg/g.

Furthermore, the ratio between the hydrophilic polymer and a detergent as well as the presence or absence of a polyalcohol is of importance for the stability of the composition.

If a polyalcohol such as mannitol is present, the weight ratio between the hydrophilic polymer and the detergent is from [18:1] to [22:1] (wt-%), e.g. [18:1], [19:1], [20:1], [21:1] or [22:1].

If the polyalcohol is absent the formulation comprises a mixture between hydrophilic polymer and a detergent, wherein the weight ratio between the hydrophilic polymer and the detergent is from [2:1] to [30:1] (wt-%), e.g. [2:1], [3:1], [4:1], [6:1], [7:1]; [8:1], [9:1], [10:1], [15:1], [20:1], [25:1] and [30:1]. In one embodiment the composition comprising 1.6 ng neurotoxic component of Botulinum toxin, 1.0 mg of hyaluronic acid, 10.0 mg of sucrose and 0.2 mg of Polysorbate 80 is excluded.

The term "production bulk composition" as used herein refers to the composition existing prior to filling of the composition into individual dosing units.

In one embodiment of the instant invention the hydrophilic polymer employed is hyaluronic acid and the detergent employed is Polysorbate 80.

In one further embodiment of the present invention the hydrophilic polymer employed is hyaluronic acid and the detergent employed is Polysorbate 20.

In one further embodiment of the present invention the hydrophilic polymer employed is polyvinylpyrolidone (PVP) and the detergent employed is Polysorbate 80.

The formulation of the invention is free of stabilising proteins.

The term "free of stabilising proteins" within the meaning of the present invention refers to formulations being free of peptides or proteins that stabilize the active peptide or protein. Examples for such excipients are, but not limited to, human serum albumin (HSA), gelatine, amino acids such as histidine, lysine, methionine or immunoglobulins.

The formulation of the instant invention is used for stabilising proteins, peptides, or mixtures thereof.

The present invention further pertains to a composition comprising said formulation and an active agent which may be a protein, a peptide, naturally occurring or modified/artificial or a mixture thereof.

The term "stable composition" as used herein relates to a composition, wherein the protein or peptide retains upon storage for at least 4 weeks at room temperature, 60% relative humidity (RH) its physical and chemical stability and integrity up to 50%, 60%, 70%, 80% and 90% compared to the value measured after lyophilisation, meaning prior to storage.

In a further embodiment, the composition of the invention is composed such that the protein or peptide retains upon storage for at least 6 months at room temperature, 60% RH its physical and chemical stability and integrity up to 50%, 60%, 70%, 80% and 90% compared to the value measured after lyophilisation, meaning prior to storage.

In a still further embodiment, the composition of the invention is composed such that the protein or peptide retains upon storage for at least 12 months at room temperature, 60% RH its physical and chemical stability and integrity up to 50%, 60%, 70%, 80% and 90% compared to the value measured after lyophilisation, meaning prior to storage.

As to the biological activity, "stable composition" refers to a composition, wherein the neurotoxic component in a reconstituted or aqueous solution of pharmaceutical composition has greater than about 20%, 30%, 40%, 50%, 60%, 70%, 80%, 90%, and up to about 100% of the toxicity that the biologically active neurotoxic component had prior to being incorporated into the pharmaceutical composition.

The term "room temperature" also designated as RT (or ambient temperature) within the meaning of the instant invention, refers to the definition of U.S. Pharmacopeia as being 20-25° C. [68-77° F.].

The term "relative humidity" also designated as RH within the meaning of the instant invention, refers to the ratio of the amount of water vapor in the air at a specific temperature to the maximum amount that the air could hold at that temperature, expressed as a percentage.

In one aspect of the invention said composition herein is stable for 7 months at 25° C. and 60% RH in lyophilised form. In another aspect of the invention said composition is stable for 3 months at 25° C. and 60% RH in lyophilised form. In one further aspect of the invention said composition is stable for 2 months at 25° C. and 60% RH in lyophilised form. In another aspect of the invention said composition is stable for 1 month at 25° C. and 60% RH in lyophilised form.

In another aspect of the invention said composition is stable for 7 months at 40° C. and 75% RH as in lyophilised form. In one further aspect of the invention said composition is stable for 3 months at 40° C. and 75% RH in lyophilised form. In one further aspect of the invention said composition is stable for 2 months at 40° C. and 75% RH in lyophilised form. In one further aspect of the invention said composition is stable for 1 month at 40° C. and 75% RH in lyophilised form.

In one embodiment of the instant invention the stability is measured by measuring the extent of aggregation as a function of time as an indicator of protein stability. In another embodiment, stability of the protein composition may be measured using the analytical methods known to the one skilled in the art by determining % of intact protein, e.g. proteolytic cleavage, cell based assay. In one further embodiment the stability of the protein composition was determined by employing a Mouse-hemidiaphragm assay (HDA-assay). In one embodiment of the instant invention HDA-assay is employed to determined the stability of the compositions claimed herein. The results are demonstrated as the potency measured in an HDA assay.

The HDA-Assay is conducted as defined by Göschel et al. ("Botulinum Toxin Therapy Neutralizing and Normeutralizing Antibodies—Therapeutic Consequences" Experimental Neurology, 1997; 147: 96-102).

The instant invention further pertains to a composition that comprises the said formulation and a peptide, a protein or a mixture thereof, being naturally occurring or modified/artificial. Modification comprises chemical modification e.g. by glycosylation, acetylation, acylation or the like, which may be beneficial e.g. to the uptake or stability of the protein. The polypeptide chain of the protein may, however, alternatively or additionally be modified by addition, substitution or deletion of one or more amino acid residues.

The term "peptide" within the meaning of the present invention refers to short polymers formed by linking in a defined order of alpha-amino acids.

The term "protein" as used herein relates to compounds of amino acids arranged in a linear chain and joined together by peptide bonds between the carboxyl and amino groups of adjacent amino acid residues. The term "protein" is used synonymously with the term "polypeptide". Proteins according to the instant invention may be artificial or naturally occurring.

The active protein or peptide in the formulation claimed herein may be artificial/modified or naturally occurring.

The term "artificial protein" within the meaning of the present invention refers to modified proteins. The term "modified protein" encompasses all possible modifications known to the person skilled in the art, e.g. chemical modification, deletion.

The term "naturally occurring" within the meaning of the present invention refers to proteins or peptides found naturally in mammal organism.

In one embodiment of the present invention, said protein is selected from the group consisting of toxins, chondroitin, elastin, actin, myosin, aprotinin, growth hormone, growth hormone releasing factor, parathyroid hormone, thyroid stimulating hormone, lipoproteins (LDL, IDL, VLDL, VHDL, HDL), apolipoproteins (ApoA-1, ApoA-II, ApoA-IV, ApoC-I, ApoC-II, ApoC-III, ApoD, ApoE), α-1 Antitrypsin, insulin, proinsullin, follicle stimulating hormone, calcitonin, oxytocin, vasopressin, leuprolide acetate, somatostatin, luteinizing hormone, glucagons, clotting factors, anti-clotting factors, plasminogen activator, human macrophage inflammatory protein, vascular endothelin growth factor (VEGF), rheumatoid factors, bone derived neurotrophic factor (BDNF), nerve growth factor-β (NGF-β), platelet-derived growth factor (PDGF), fibroblast growth factor (FGF), epidermal growth factor (EGF), transforming growth factor (TGF-β1, TGF-β2, TGF-β3, TGF-β4, TGF-β5), erythropoietin, interleukins (IL-1 to IL-10), bone morphogenic protein (BMP) parathyroid hormone, DNAse, cationic ferritin, interferon (α, β, γ) and mixtures thereof.

In another embodiment of the present invention said protein is a toxin. In one further embodiment of the instant invention said toxin is, a Botulinum toxin, a diphtheria toxin or a tetanus toxin, or a mixture of two or more thereof.

In one embodiment of the present invention the protein in the said composition is Botulinum toxin.

In one further embodiment of the instant invention said Botulinum toxin is selected from the group consisting of type A, B, C, $C_1$, D, E, F and G. In another embodiment of the present invention said Botulinum toxin is type A. In one further embodiment of the instant invention said protein is the neurotoxic component of Botulinum toxin type A.

The term "Botulinum toxin" as used throughout the present application, refers to the neurotoxic component devoid of any other Clostridial proteins, but also to the "Botulinum toxin complex". The term "Botulinum toxin" is used herein in cases when no discrimination between the toxin complex and the neurotoxic component is necessary or desired. "BoNT" or "NT" are commonly used abbreviations.

The "neurotoxic component" of the botulinum toxin complex is initially formed as a single polypeptide chain, having in the case of serotype A a molecular weight of approximately 150 kDa. In other serotypes the neurotoxic component has been observed to vary between about 145 and about 170 kDa, depending on the bacterial source. In the case of serotype A, for example, proteolytic processing of the polypeptide results in an activated polypeptide in the form of a dichain polypeptide consisting of a heavy chain and a light chain, which are linked by a disulfide bond. In humans, the heavy chain mediates binding to pre-synaptic cholinergic nerve terminals and internalization of the toxin into the cell. The term "neurotoxic component" also includes functional homologs found in the other serotypes of *Clostridium botulinum*. In one embodiment of the present invention, the neurotoxic component is devoid of any other *C. botulinum* protein, e.g. also devoid of RNA, which might potentially be associated with the neurotoxic component. The neurotoxic component may be the single chain precursor protein of approximately 150 kDa or the proteolytically processed neurotoxic component, comprising the light chain (Lc) of approximately 50 kDa and the heavy chain (Hc) of approximately 100 kDa, which may be linked by one or more disulfide bonds (for a review see e.g. Simpson L L, Ann Rev Pharmacol Toxicol. 2004; 44:167-93). In humans, the heavy chain mediates binding to pre-synaptic cholinergic nerve terminals and internalization of the toxin into the cell. The light chain is believed to be responsible for the toxic effects, acting as zinc-endopeptidase and cleaving specific proteins responsible for membrane fusion (SNARE complex) (see e.g. Montecucco C., Shiavo G., Rosetto O. The mechanism of action of tetanus and Botulinum neurotoxins. Arch Toxicol. 1996; 18 (Suppl.): 342-354)).

The neurotoxic subunit of the Botulinum toxin complex is referred in this document as the "neurotoxic component" or the "neurotoxic component free of complexing proteins". The production of the neurotoxic component of Botulinum toxin type A and B are described, for example, in the international patent application WO 00/74703.

In a further embodiment the Botulinum toxin is Botulinum toxin type A. In one embodiment said Botulinum toxin is free of any complexing proteins (neurotoxic component). In one further embodiment it is the pure neurotoxic component serotype A. In addition thereto, modified as well as recombinant produced neurotoxic components of Botulinum toxins including the respective mutations, deletions, etc. are also within the scope of the present invention. With respect to suitable mutants, reference is made to WO 2006/027207 A1, WO 2009/015840 A1, WO 2006/114308 A1 and EP 08015287.9 which are fully incorporated by reference herein. Furthermore, within the present invention, mixtures of various serotypes (in the form the neurotoxic component or recombinant form or both forms thereof, e.g. mixtures of Botulinum neurotoxins of types A and B) may be used. The present invention, however, also refers to toxins, e.g. Botulinum toxins, which are chemically modified, e.g. by pegylation, glycosylation, sulfatation, phosphorylation or any other modification, in particular of one or more surface or solvent exposed amino acid(s). Such Botulinum toxins are disclosed in e.g. EP 08015288.7 and the prior art disclosed therein.

In accordance with the teaching of the present invention, it also encompasses that the medicament contains no proteins found in the Botulinum toxin complex other than the neurotoxic component.

The Botulinum toxin, preferably the neurotoxic component referred to herein, may be the sole active component or may contain additional pharmaceutically active components.

In one embodiment the composition is lyophilized.

In one embodiment of the instant invention, the liquid compositions can be filled into lyo-vials and subsequently lyophilized. Lyophilisation of the samples is conducted by freezing the samples at temperatures between $-35°$ C. to $-65°$ C. for a period of from 1 to 10 hours, e.g. 5 to 10 hours. This step is followed by primary drying at a shelf temperature of $-30°$ C. to $10°$ C., e.g. $-20°$ C. to $10°$ C. or $5°$ C. to $10°$ C. under a pressure of 100 mTorr to 200 mTorr for a period of 10 hours to 25 hours. Finally, the samples enter the last step of the lyophilisation process, being secondary drying, which is conducted at a shelf temperature of $15°$ C. to $25°$ C. for 5 hours to 15 hours. Sample volume in the lyo-vials varies between 0.1 to 5 ml, e.g. 0.2 to 1 ml or 0.4 to 0.6 ml, or 0.5 ml. In one embodiment sample volume is between 2 ml to 4 ml.

In one further embodiment of the present invention, the lyophilisation process can be conducted by freezing the samples at a shelf temperature of $-45°$ C. for about 2 hours followed by primary drying at a shelf temperature of $-25°$ C. and 90 mTorr for 12 hours, and secondary drying at a shelf temperature of $25°$ C. for 12.5 hours.

In one embodiment an injectable solution comprising the said composition is claimed.

The injectable solution claimed herein is stable at a temperature of 2 to $8°$ C. for 24 hours.

In one embodiment said injectable solution is obtained by reconstituting said lyophilised composition with a pharmaceutically acceptable sterile solvent prior to administration to a mammal.

In one further embodiment, the present invention relates to a process for the preparation of said injectable solution designed for intravenous, subcutaneous, intramuscular, intraarticular, intraperitoneal, intracerobrospinal, intracardiac, intrathecal, intravesical, intraosseous, intravitreal, epidural, intrasynovial injection into a mammal. Said process comprises the step of dissolving the said lyophilised composition as claimed herein, prior to administration, in a pharmaceutical acceptable sterile solvent.

In another embodiment of the instant invention, said injectable solution is also administered via other routes of administration. Such routes of administration are, but not limited to, inhalation, oral and nasal. An example for such an application is, but not limited to, for instance, inhalation of α-1 Antitrypsin by COPD patients in form of an injectable solution as claimed herein.

The composition as claimed herein is for use as a medicament, a cosmetic product, a cosmoceutical product or a diagnostic product.

The term "medicament" as used herein relates to a product or a mixture of products, wherein said products may be mixed prior to administration or be used one after another and have a therapeutical and/or diagnostic outcome on the mammal they are administered to.

The term "cosmetic product" as used herein relates to products employed for cosmetic purposes. The term "cosmetic" as used herein relates to products as defined in the FD&C Act, sec. 201(i) (*Federal Food, Drug and Cosmetic Act, FDA*) as intended to be rubbed, poured, sprinkled, or sprayed on, introduced into, or otherwise applied to the human body for cleansing, beautifying, promoting attractiveness, or altering the appearance".

The term "diagnostic product" as used herein relates to any product comprising any compound or compounds that is delivered to a patient in order to carry out a diagnostic test or assay on the patient.

The term "cosmeceutical product" as used herein relates to a non-prescription cosmetic product, that has also medicinal or drug-like benefits.

In one embodiment of the present invention the claimed formulation herein may comprise a buffer.

The term "buffer" as used herein relates to an aqueous solution consisting of a mixture of a weak acid and its conjugate base or a weak base and its conjugate acid.

In one further embodiment of the present invention the buffer is selected from the group consisting of phosphate buffer, acetate buffer, citrate buffer, formate buffer, benzoate buffer, TRIS (Tris-(hydroxymethyl)-aminomethan) and maleate buffer. Said buffer is prepared according to the specifications of USP (United States Pharmacopoeia), EP (European Pharmacopoeia) and the JP (Japanese Pharmacopoeia) by using Pharmacopoeia-conform excipients. The buffer concentration is to be determined in regard to the pH of the end product.

The excipients and the actives (peptides and/or proteins) employed in the formulation herein are pharmaceutically acceptable.

The term "pharmaceutically acceptable" as used herein relates to any excipient, pharmaceutically active ingredient, which enables the said composition to be taken by mammals at therapeutically effective concentration, avoiding any kind of side effects.

In one aspect the present invention pertains to a kit comprising one or more containers comprising the formulation/composition and instructions for use of the formulation/composition and optionally a pharmaceutically acceptable sterile solvent.

The term "solvent" as used herein relates to any liquid which aids in dissolving or diluting any other substance or substance mixture or a product. The term "solvent" within the meaning of the instant invention may encompass also a mixture of solvents.

The pharmaceutical acceptable sterile solvent to be employed within said process is, but not limited to, water for injection (WFI), isotonic salt solution, Ringer's solution, pH-buffered solution, an aqueous solution of 5% glucose.

A further aspect of the present invention relates to a sterile composition.

The term "sterile" as used herein relates to the absence of undesired microorganisms and relates to the norms defined in the USP (United States Pharmacopoeia), EP (European Pharmacopoeia) and the JP (Japanese Pharmacopoeia).

In one embodiment the composition is non-pyrogenic e.g. containing <1 EU (endotoxin unit, a standard measure) per dose, and preferably <0.1 EU per dose. In one further embodiment said injectable solution is also sterile and non-pyrogenic.

In one embodiment of the instant invention said composition is for use in vertebrates, such as mammals.

The term "vertebrate" is defined herein as any member of the subphylum vertebrate, chordates with backbones or spinal columns. Therefore the term "vertebrate" encompasses humans, mammals, marsupials, reptiles, birds, amphibians and fish.

The term "mammal" in this document is defined as any warm-blooded, vertebrate characterized by the presence of sweat glands, including milk producing glands, and by the presence of hair, three middle ear bones used in hearing, and a neocortex region in the brain. A male or female human, dog, cat, pig, cow, horse, donkey, sheep, goat and deer is therefore encompassed by this definition of a mammal.

The term "marsupial" is defined herein as a mammal in which the female typically has a pouch in which it rears its young through early infancy. They differ from placental mammals in their reproductive traits.

The term "reptile" is defined herein as any air-breathing, ectothermic vertebrate that has skin covered in scales as opposed to hair or feathers.

The term "bird" is defined herein as any bipedal, warm-blooded, vertebrate that lays eggs.

The term "amphibian" is defined herein as all living tetrapods (four-legged vertebrates) that do not have amniotic eggs, are ectothermic and generally spend part of their time on land.

The term "fish" is defined herein as aquatic vertebrates that are typically ectothermic, covered with scales, and equipped with two sets of paired fins and several unpaired fins.

The concentration values herein are expressed in "about" values.

The term "about" as used herein is intended to reflect a variation of 20% of the value it is attached to.

The instant invention further relates to a process for preparing the said composition characterized in that said composition is prepared as an aqueous composition and subsequently lyophilized.

Prior to lyophilisation, the protein or peptide is dissolved in an aqueous solution, which is stabilized by a hydrophilic polymer, a mixture of polyalcohol and a sugar, a detergent. The stabilization of the protein in solution means that the protein is enveloped by a structure composed of hydrophilic polymer, a detergent and a mixture of polyalcohol and sugar.

By using a detergent, it is possible to reduce the amount of hydrophilic polymers. In one embodiment by using Tween 80 the concentration of PVP was reduced from 150 mg/g to 80 mg/g based on the total weight of production bulk composition. Due to such an effect, the industrial production of the composition herein was improved.

In one embodiment of the present invention the composition herein comprises the neurotoxic component of Botulinum toxin in a quantity of about 2 pg to 50 ng per 1 g production bulk composition. Preferred quantity ranges are in the range of from 2 pg to 200 pg, 200 pg to 400 pg, 400 pg to 600 pg, 600 pg to 800 pg, 800 pg to 1 ng, 1 ng to 1.5 ng, 1.5 ng to 2 ng, 2 ng to 2.5 ng, 2.5 ng to 3 ng, 3 to 3.5 ng, 3.5 to 4 ng, 4 ng to 4.5 ng, and 4.5 to 5 ng per 1 g of water, respectively per 1 g production bulk composition. In an embodiment of the instant invention, the neurotoxic component has a biological activity of 50 to 250 $LD_{50}$ units per ng neurotoxic component, as determined in a mouse $LD_{50}$ assay. In one further embodiment, the neurotoxic component has a biological activity of about 150 $LD_{50}$ per ng neurotoxic component. In one further embodiment 1.6 ng of neurotoxin relate to 100 $LD_{50}$ units.

In some embodiments a starting-activity of the formulation of 10 to 400 $LD_{50}$ units is envisaged, in further embodiments a starting-activity of the formulation of 50-200 $LD_{50}$ units is envisaged, in one further embodiment 200 $LD_{50}$ units and in another embodiment 100 $LD_{50}$ units.

The following demonstrates some embodiments of the stable compositions as claimed herein, wherein the amounts of the constituents specified are all relative to 1 g production bulk composition.

In one embodiment of the present invention, the composition claimed herein comprises ≤1.6 ng/g neurotoxic component of Botulinum toxin, about 2 mg/g of hyaluronic acid, about 30 mg/g of mannitol, about 10 mg/g of sucrose and about 0.1 mg/g of Polysorbate 80.

In another embodiment of the present invention, the composition claimed herein comprises ≤1.6 ng/g neurotoxic component of Botulinum toxin, about 1.0 mg/g of hyaluronic acid, no mannitol or other polyalcohol such as mannitol, inositol, lactitol, isomalt, xylitol, erythritol and sorbitol, about 10.0 mg/g of sucrose and about 0.2 mg of Polysorbate 80.

Composition as claimed herein is for treatment of a disease or condition caused by or associated with hyperactive cholinergic innervation of muscles or exocrine glands in a patient, where the neurotoxic component blocks acetylcholine secretion into the synaptic cleft. Therefore, the composition claimed by the present invention may be directed to the treatment of any of the following indications, most of which are described in detail in Dressler D (2000) (Botulinum Toxin Therapy. Thieme Verlag, Stuttgart, N.Y.):

dystonia
  cranial dystonia
    blepharospasm
    oromandibular dystonia
      jaw opening type
      jaw closing type
    bruxism
    Meige syndrome
    lingual dystonia
    apraxia of eyelid opening
  cervical dystonia
    antecollis
    retrocollis
    laterocollis
    torticollis
  pharyngeal dystonia
  laryngeal dystonia
    spasmodic dysphonia/adductor type
    spasmodic dysphonia/abductor type
    spasmodic dyspnea
  limb dystonia
    arm dystonia
      task specific dystonia
        writer's cramp
        musician's cramps
        golfer's cramp
    leg dystonia
      thigh adduction, thigh abduction
      knee flexion, knee extension
      ankle flexion, ankle extension
      equinovarus deformity
    foot dystonia
      striatal toe
      toe flexion
      toe extension
    axial dystonia
      pisa syndrome
      belly dancer dystonia
    segmental dystonia
    hemidystonia
    generalised dystonia
  dystonia in lubag
  dystonia in corticobasal degeneration
  dystonia in lubag
  tardive dystonia
  dystonia in spinocerebellar ataxia
  dystonia in Parkinson's disease
  dystonia in Huntington's disease
  dystonia in Hallervorden Spatz disease
  dopa-induced dyskinesias/dopa-induced dystonia
  tardive dyskinesias/tardive dystonia
  paroxysmal dyskinesias/dystonias
    kinesiogenic
    non-kinesiogenic
    action-induced
  palatal myoclonus
  myoclonus
  myokymia
  rigidity
  benign muscle cramps
  hereditary chin trembling
  paradoxic jaw muscle activity
  hemimasticatory spasms
  hypertrophic branchial myopathy
  maseteric hypertrophy
  tibialis anterior hypertrophy
  nystagmus
  oscillopsia
  supranuclear gaze palsy
  epilepsia partialis continua
  planning of spasmodic torticollis operation
  abductor vocal cord paralysis
  recalcitant mutational dysphonia
  upper oesophageal sphincter dysfunction
  vocal fold granuloma
  stuttering
  Gilles de la Tourette syndrome
  middle ear myoclonus
  protective larynx closure
  postlaryngectomy speech failure
  protective ptosis
  entropion
  sphincter Odii dysfunction
  pseudoachalasia
  nonachalsia oesophageal motor disorders
  vaginismus
  postoperative immobilisation
  tremor
  bladder dysfunction
  detrusor sphincter dyssynergia
  bladder sphincter spasm
  hemifacial spasm
  reinnervation dyskinesias
  cosmetic use
  craw's feet
  frowning
  facial asymmetries
  mentalis dimples
  stiff person syndrome
  tetanus
  prostate hyperplasia
  adipositas treatment
  infantile cerebral palsy
  strabismus
    mixed
    paralytic
    concomitant
    after retinal detachment surgery
    after cataract surgery
    in aphakia
    myositic strabismus
    myopathic strabismus
    dissociated vertical deviation
    as an adjunct to strabismus surgery
    esotropia
    exotropia
  achalasia
  anal fissures
  exocrine gland hyperactivity
  Frey syndrome
  Crocodile Tears syndrome
  hyperhidrosis
    axillar
    palmar
    plantar
  rhinorrhea
  relative hypersalivation
    in stroke
    in parkinsosn's
    in amyotrophic lateral sclerosis spastic conditions
  in encephalitis and myelitis
    autoimmune processes
      multiple sclerosis
      transverse myelitis
      Devic syndrome
    viral infections
    bacterial infections
    parasitic infections
    fungal infections
  in hereditary spastic paraparesis
  postapoplectic syndrome
    hemispheric infarction
    brainstem infarction
    myelon infarction
  in central nervous system trauma
    hemispheric lesions
    brainstem lesions
    myelon lesion
  in central nervous system hemorrhage
    intracerebral hemorrhage
    subarachnoidal hemorrhage
    subdural hemorrhage
    intraspinal hemorrhage
  in neoplasias
    hemispheric tumors
    brainstem tumors
    myelon tumors In another embodiment, the present invention pertains to a kit, wherein said kit comprises one or more of a container comprising the formulation/composition claimed herein, instructions for reconstituting the said formulation/composition and optionally, a pharmaceutically acceptable sterile solvent. Suitable containers include, but are not limited to, single vials, dual chamber vials, single application syringes or dual chamber syringes. The container may be formed from a variety of material such as glass or plastic adapted for pharmaceutical, diagnostic, cosmetic or cosmeceutical administration. The said kit may be adapted for single use or for multiple uses.

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1

Studies were conducted to find a stabilized composition of Botulinum toxin type A. Each composition comprised of ≤1.6 ng (respectively 100 $LD_{50}$ units) neurotoxic component of Botulinum toxin type A. The composition is summarized in the following table, wherein the amounts are given as mg per 1 g of the production bulk composition.

| Composition No. | Hyaluronic acid [mg/g] | Mannitol [mg/g] | Sucrose [mg/g] | Polysorbate 80 [mg/g] |
|---|---|---|---|---|
| Comparative Composition 1 | 1 | 20 | 10 | 0.2 |
| Comparative Composition 2 | 1 | 30 | 10 | 0.1 |
| Example 1 | 2 | 30 | 10 | 0.1 |

The stability of the compositions were determined by using a $LD_{50}$-assay as defined by Göschel et al. ("*Botulinum Toxin Therapy: Neutralizing and Normeutralizing Antibodies—Therapeutic Consequences*" Experimental Neurology, 1997; 147: 96-102). The start value was measured after lyophilisation.

It becomes apparent that a fine relationship of the different ingredients exists, which results in a stable or unstable compositions.

Example 2

Further studies were conducted to find a stabilized composition of Botulinum toxin type A without a polyalcohol. Each composition comprised of ≤1.6 ng (respectively 100 $LD_{50}$ units) neurotoxic component of Botulinum toxin type A. In another embodiment an amount of ≤3.2 ng (respectively 200 $LD_{50}$ units) neurotoxic component of Botulinum toxin type is envisaged.

The example-composition s were produced at 5° C., 18° C. or 30° C., respectively. Then they were lyophilized each and stored at 25° C. and 60% relative humidity. The stability during storage was tested by reconstituting the solution according to standard protocol and testing its $LD_{50}$-activity according to Göschel et al. ("*Botulinum Toxin Therapy: Neutralizing and Normeutralizing Antibodies—Therapeutic Consequences*" Experimental Neurology, 1997; 147: 96-102). The start value was measured after lyophilisation. All of the example-compositions 2a, 2b and 2c were stable (i.e. showed an $LD_{50}$ of at least 90%) even after 12 month of storage.

The composition of the screening formulations is summarized in the table below. There the amount of the neurotoxic component of Botulinum toxin type A is 1.6 ng (respectively 100 $LD_{50}$ units) and the amounts for the other compounds are given as mg per 1 g of the production bulk composition.

| Composition No. | Production T [° C.] | Hyaluronic acid [mg/g] | Mannitol [mg/g] | Sucrose [mg/g] | Polysorbate 80 [mg/g] | Stability |
|---|---|---|---|---|---|---|
| Example 2a | 5° C. | 1 | 0 | 10 | 0.2 | at least 90% of starting $LD_{50}$ after ≥12 month |

-continued

| Composition No. | Production T [° C.] | Hyaluronic acid [mg/g] | Mannitol [mg/g] | Sucrose [mg/g] | Polysorbate 80 [mg/g] | Stability |
|---|---|---|---|---|---|---|
| Example 2b | 18° C. | 1 | 0 | 10 | 0.2 | at least 90% of starting $LD_{50}$ after ≥12 month |
| Example 2c | 30° C. | 1 | 0 | 10 | 0.2 | at least 90% of starting $LD_{50}$ after ≥12 month |

It becomes apparent that polyalcohol-free compositions comprise a quite high stability

FIGURES

FIG. 1:

The example-composition as well as the comparative f compositions were produced at 5° C., lyophilized and stored at 25° C. and 60% relative humidity. The stability during storage was tested by reconstituting the solution according to standard protocol and testing its $LD_{50}$-activity according to Göschel et al. ("*Botulinum Toxin Therapy Neutralizing and Normeutralizing Antibodies—Therapeutic Consequences*" Experimental Neurology, 1997; 147: 96-102). Whereas the example-formulation 1 was stable (i.e. showed an $LD_{50}$ of at least 90%) even after 12 month of storage, whereas the activity of the comparative compositions decayed quite rapidly.

FIG. 2:

The example-composition as well as the comparative compositions were produced at 18° C., lyophilized and stored at 25° C. and 60% relative humidity. The stability during storage was tested by reconstituting the solution according to standard protocol and testing its $LD_{50}$-activity according to Göschel et al. ("*Botulinum Toxin Therapy Neutralizing and Normeutralizing Antibodies—Therapeutic Consequences*" Experimental Neurology, 1997; 147: 96-102). Whereas the example-composition 1 was stable (i.e. showed an $LD_{50}$ of at least 90%) even after 12 month of storage, whereas the activity of the comparative compositions decayed quite rapidly.

The invention claimed is:

1. A formulation free of proteins comprising, (a) a hydrophilic polymer;

(b) a sugar;

(c) a non-ionic detergent; and (d) a polyalcohol, wherein the weight ratio of polyalcohol to sugar is from 2:1 to 5:1 (wt-%), wherein the weight ratio between the hydrophilic polymer and the non-ionic detergent is from 18:1 to 22:1 (wt-%), and wherein the non-ionic detergent is present in said formulation in an amount between 0.2 and 0.01 mg/g.

2. A formulation free of proteins comprising, (a) a hydrophilic polymer;

(b) a sugar; and (c) a non-ionic detergent, wherein the weight ratio between the hydrophilic polymer and the non-ionic detergent is from 2:1 to 30:1 (wt-%), and wherein the non-ionic detergent is present in the formulation in an amount between 0.2 and 0.01 mg/g, and wherein no polyalcohol is present.

3. The formulation of claim 1, wherein the hydrophilic polymer is selected from the group consisting of hyaluronic acid, polyvinylpyrollidone (PVP), copolymers of N-vinylpyrollidone, a cellulose derivative, Polyethyleneglycol (PEG), PEG/PPG block copolymers, homo- and copolymers of acrylic and methacrylic acid, polyurethanes, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, and mixtures thereof.

4. The formulation of claim 1, wherein the polyalcohol is selected from the group consisting of mannitol, inositol, lactilol, isomalt, xylitol, erythritol, sorbitol, and mixtures thereof.

5. The formulation of claim 1, wherein the sugar is selected from the group consisting of monosaccharides, disaccharides, polysaccharides, and mixtures thereof.

6. The formulation of claim 1, which is in the form of a composition further comprising a pharmaceutically active peptide, a protein or a mixture thereof.

7. The composition of claim 6, which is lyophilized.

8. The composition of claim 6, wherein said pharmaceutically active protein is selected from the group consisting of toxins, chondroitin, elastin, actin, myosin, aprotinin, growth hormone, growth hormone releasing factor, parathyroid hormone, thyroid stimulating hormone, lipoproteins (LDL, IDL, VLDL, VHDL, HDL), apolipoproteins (ApoA-1, ApoA-II, ApoA-IV, ApoC-I, ApoC-II, ApoC-III, ApoD, ApoE), α-1 Antitrypsin, insulin, proinsulin, follicle stimulating hormone, calcitonin, oxytocin, vasopressin, leuprolide acetate, somatostatin, luteinizing hormone, glucagons, clotting factors, anti-clotting factors, plasminogen activator, human macrophage inflammatory protein, vascular endothelin growth factor (VEGF), rheumatoid factors, Done derived neurotrophic factor (BDNF), nerve growth factor-β (NGF-β), platelet-derived growth factor (PDGF), fibroblast growth factor (FGF), epidermal growth factor (EGF), transforming growth factor (TGF-β1, TGF-β2, TGF-β3, TGE-β4, TGE-β5), erythropoietin, interleukins (IL-1 to IL-10), bone morphogenic protein (BMP) parathyroid hormone, DNAse, cationic ferritin, interferon α, interferon β, interferon γ, and mixtures thereof.

9. The composition of claim 6, wherein the pharmaceutically active protein is selected from the group consisting of Botulinum toxin, diphtheria toxin, tetanus toxin and mixtures thereof.

10. The composition of claim 9, which comprises botulinum toxin, hyaluronic acid, mannitol, sucrose, polysorbate 80 and, optionally, water for injection.

11. The composition of claim 6, which is comprised in a medicament, a cosmetic product, a cosmeceutical product or a diagnostic product.

12. An injectable solution comprising the composition of claim 11.

13. A kit comprising, (a) one or more containers comprising the composition of claim 6; and (b) instructions for use of the composition.

14. A method for stabilizing pharmaceutically active proteins, peptides, or mixtures thereof, comprising admixing such pharmaceutically active protein, peptide, or a mixture thereof, with the formulation of claim 1.

15. The kit of claim 13, further comprising a container of a pharmaceutically acceptable sterile solvent selected from the group consisting of water for injection, isotonic salt solution, Ringer's solution, pH-buffered solution, an aqueous solution of 5% glucose, and mixtures thereof.

* * * * *